United States Patent
Bowley et al.

(10) Patent No.: US 10,449,034 B2
(45) Date of Patent: *Oct. 22, 2019

(54) GRAFT MATERIALS FOR SURGICAL BREAST PROCEDURES

(71) Applicant: LifeCell Corporation, Branchburg, NJ (US)

(72) Inventors: Melissa Richter Bowley, Newport, RI (US); Aaron Barere, Hoboken, NJ (US); Evan Friedman, Montvale, NJ (US); Nathaniel Bachrach, Clifton, NJ (US)

(73) Assignee: LifeCell Corporation, Branchburg, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/620,667

(22) Filed: Feb. 12, 2015

(65) Prior Publication Data

US 2015/0157451 A1 Jun. 11, 2015

Related U.S. Application Data

(63) Continuation of application No. 12/506,839, filed on Jul. 21, 2009, now Pat. No. 8,986,377.

(51) Int. Cl.
*A61F 2/12* (2006.01)
*A61L 27/36* (2006.01)
*A61F 2/00* (2006.01)

(52) U.S. Cl.
CPC .............. *A61F 2/12* (2013.01); *A61L 27/362* (2013.01); *A61L 27/3695* (2013.01); *A61F 2/0063* (2013.01); *A61F 2210/0004* (2013.01); *A61F 2230/0008* (2013.01); *A61F 2310/00365* (2013.01); *A61L 27/3637* (2013.01); *A61L 27/3683* (2013.01); *A61L 2430/04* (2013.01); *Y10T 29/49995* (2015.01)

(58) Field of Classification Search
CPC .. A61F 2/12; A61F 2/52; A61F 2/0059; A61F 2/0063; A61F 2/0068; A61F 2/105; A61L 2430/04; A61B 19/24; A61B 19/02; A61B 2017/00796
See application file for complete search history.

(56) References Cited

U.S. PATENT DOCUMENTS

| | | | |
|---|---|---|---|
| 2,108,205 A | * | 2/1938 | Martin .................. A41C 3/10 623/7 |
| 3,683,424 A | | 8/1972 | Pangman |
| 4,298,998 A | | 11/1981 | Naficy |

(Continued)

FOREIGN PATENT DOCUMENTS

| CN | 1953657 A | 4/2007 |
|---|---|---|
| DE | 102006029605 A1 | 12/2007 |

(Continued)

OTHER PUBLICATIONS

Pope, Eric R., "Mesh Skin Grafting", Veterinary Clinics of North America: Small Animal Practice, vol. 20, No. 1, pp. 177-187 (Jan. 1990).

(Continued)

*Primary Examiner* — Dinah Baria

(57) ABSTRACT

Graft materials and devices for surgical breast procedures, as well as methods of making graft devices, are described.

13 Claims, 8 Drawing Sheets

(56) References Cited

U.S. PATENT DOCUMENTS

| | | | |
|---|---|---|---|
| 4,840,629 | A | 6/1989 | Bustos |
| 4,936,858 | A | 6/1990 | O'Keeffe |
| 5,356,429 | A | 10/1994 | Seare |
| 5,584,884 | A | 12/1996 | Pignataro |
| 5,658,328 | A | 8/1997 | Johnson |
| 5,658,330 | A | 8/1997 | Carlisle et al. |
| 5,676,161 | A | 10/1997 | Breiner |
| 5,713,959 | A | 2/1998 | Bartlett et al. |
| 5,733,337 | A | 3/1998 | Carr, Jr. et al. |
| 5,755,791 | A | 5/1998 | Whitson et al. |
| 5,954,767 | A | 9/1999 | Pajotin et al. |
| 5,968,096 | A | 10/1999 | Whitson et al. |
| 5,997,575 | A | 12/1999 | Whitson et al. |
| 6,099,566 | A | 8/2000 | Vonderharr et al. |
| 6,203,570 | B1 | 3/2001 | Baeke |
| 6,210,439 | B1 | 4/2001 | Firmin et al. |
| 6,334,868 | B1 | 1/2002 | Ham |
| 6,368,541 | B1 | 4/2002 | Pajotin et al. |
| 6,638,308 | B2 | 10/2003 | Corbitt, Jr. et al. |
| 6,666,892 | B2 | 12/2003 | Hiles et al. |
| 6,723,133 | B1 | 4/2004 | Pajotin |
| 6,736,823 | B2 | 5/2004 | Darois et al. |
| 6,736,854 | B2 | 5/2004 | Vadurro et al. |
| 6,740,122 | B1 | 5/2004 | Pajotin |
| 6,802,861 | B1 | 10/2004 | Hamas |
| 7,011,688 | B2 | 3/2006 | Gryska et al. |
| 7,081,135 | B2 | 7/2006 | Smith et al. |
| 7,476,249 | B2 | 1/2009 | Frank |
| 7,699,895 | B2 | 4/2010 | Hiles et al. |
| 7,875,074 | B2 | 1/2011 | Chen et al. |
| 8,007,531 | B2 | 8/2011 | Frank |
| 8,128,708 | B2 | 3/2012 | Hiles et al. |
| 8,858,647 | B2 | 10/2014 | Markman |
| 2001/0041936 | A1 | 11/2001 | Corbitt, Jr. et al. |
| 2002/0103542 | A1 | 8/2002 | Bilbo |
| 2003/0130747 | A1 | 7/2003 | Abraham et al. |
| 2003/0212461 | A1 | 11/2003 | Vadurro et al. |
| 2003/0212462 | A1 | 11/2003 | Gryska et al. |
| 2004/0049269 | A1 | 3/2004 | Corbitt, Jr. et al. |
| 2004/0260315 | A1 | 12/2004 | Dell et al. |
| 2005/0021141 | A1 | 1/2005 | Bleyer et al. |
| 2005/0165425 | A1 | 7/2005 | Croce et al. |
| 2005/0187624 | A1 | 8/2005 | Corbitt, Jr. |
| 2005/0250977 | A1 | 11/2005 | Montpetit et al. |
| 2005/0260176 | A1 | 11/2005 | Ayares et al. |
| 2006/0030939 | A1 | 2/2006 | Frank |
| 2006/0167338 | A1 | 7/2006 | Shafaram |
| 2007/0038299 | A1 | 2/2007 | Stone et al. |
| 2007/0088434 | A1 | 4/2007 | Frank |
| 2007/0116678 | A1 | 5/2007 | Sung et al. |
| 2007/0250177 | A1 | 10/2007 | Bilbo |
| 2008/0027273 | A1 | 1/2008 | Gutterman |
| 2008/0082113 | A1 | 4/2008 | Bishop et al. |
| 2008/0097601 | A1 | 4/2008 | Codori-Hurff et al. |
| 2008/0108134 | A1 | 5/2008 | Murphy et al. |
| 2008/0167729 | A1 | 7/2008 | Nelson et al. |
| 2008/0260853 | A1 | 10/2008 | Firestone |
| 2008/0281418 | A1 | 11/2008 | Firestone |
| 2008/0281419 | A1 | 11/2008 | Matheny et al. |
| 2009/0024227 | A1 | 1/2009 | Lesh |
| 2009/0024228 | A1 | 1/2009 | Lesh |
| 2009/0082864 | A1 | 3/2009 | Chen |
| 2009/0125107 | A1 | 5/2009 | Maxwell |
| 2009/0198332 | A1 | 8/2009 | Becker |
| 2009/0216338 | A1 | 8/2009 | Gingras et al. |
| 2009/0240342 | A1 | 9/2009 | Lindh et al. |
| 2010/0010627 | A1 | 1/2010 | Matheny |
| 2010/0023029 | A1 | 1/2010 | Young |
| 2010/0191330 | A1 | 7/2010 | Lauryssen et al. |
| 2010/0217388 | A1 | 8/2010 | Cohen et al. |
| 2011/0035004 | A1 | 2/2011 | Maxwell |
| 2011/0276039 | A1 | 11/2011 | Markman |
| 2012/0158134 | A1 | 6/2012 | Codori-Hurff et al. |
| 2013/0085579 | A1 | 4/2013 | Markman |

FOREIGN PATENT DOCUMENTS

| | | | | |
|---|---|---|---|---|
| FR | 2682284 | A1 * | 4/1993 | ............... A61F 2/12 |
| FR | 2746298 | A1 * | 9/1997 | ........... A61F 2/0059 |
| JP | 09-47503 | | 2/1997 | |
| JP | 10-158906 | | 6/1998 | |
| JP | 2005-536228 | | 12/2005 | |
| WO | WO 2004/096098 | | 11/2004 | |
| WO | WO 2005/089411 | | 9/2005 | |
| WO | WO 2006/115892 | | 11/2006 | |
| WO | WO 2006/135998 | | 12/2006 | |
| WO | WO 2007/004214 | | 1/2007 | |
| WO | WO 2007/134134 | | 11/2007 | |
| WO | WO 2008/016919 | | 2/2008 | |
| WO | WO 2008/121816 | | 10/2008 | |
| WO | WO 2009/001293 | | 12/2008 | |
| WO | WO 2009/065013 | | 5/2009 | |

OTHER PUBLICATIONS

Goes, Joao C.S., "Periareolar Mammaplasty: Double Skin Technique with Application of Polygractine 910 Mesh", Rev. Soc. Bras. Cir. Plast. Estet. Reconstr., 7(1, 2, 3) (1992).

Goes, Joao C.S., "Periareolar Mammaplasty: Double Skin Technique with Application of Polyglactine or Mixed Mesh", Plastic and Reconstructive Surgery (Apr. 1996).

Goes, Joao C.S., "Periareolar Mammaplasty With Mixed Mesh Support: The Double Skin Technique", Operative Techniques in Plastic and Reconstructive Surgery, vol. 3, No. 3, pp. 199-206 (Aug. 1996).

Goes, Joao C.S., "Periareolar Mastopexy and Reduction with Mesh Support, Double Skin Technique", Surgery of the Breast: Principles and Art, 697 (1998).

Goes, Joao C.S., "Periareolar Mastopexy: Double Skin Technique with Mesh Support", Aesthetic Surgery Journal, (Mar./Apr. 2003).

Baxter, R.A., "Intracapsular Allogenic Dermal Grafts for Breast Implant-Related Problems", Plast. Reconstr. Surg., 112(6): 1692-1696 (2003).

Goes, Joao C.S. et al., "The Application of Mesh Support in Periareolar Breast Surgery: Clinical and Mammographic Evaluation", Aesth. Plast. Surg., 28:268-274 (2004).

Breuing, K.H. et al., "Immediate Bilateral Breast Reconstruction With Implants and Inferolateral AlloDerm Slings", Annals of Plastic Surgery, 55(3): 232-239 (2005).

Breuing, K.H. et al., "Inferolateral AlloDerm Hammock for Implant Coverage in Breast Cadaveric Dermal Slings", Annals of Plastic Surgery, 59(3): 250-255 (2007).

Bindingnavele et al., "Use of acellular cadaveric dermis and tissue expansion in postmastectomy breast reconstruction", Journal of Plastic, Reconstructive, and Aesthetic Surgery, 60(2007): 1214-1218.

Colwell, A.S. et al., "Improving Shape and Symmetry in Mastopexy With Autologous or Cadaveric Dermal Slings", Annals of Plastic Surgery, 61(2): 138-142 (2008).

Darcy, C.M., "A Technique for Preparing Meshed Skin Grafts With Planned Expansion Ratios", British Journal of Plastic Surgery, 56(1): 77-79 (2003).

Duncan, D.I., "Correction of Implant Rippling Using Allograft Dermis", Aesthetic Surgery Journal, 21(1): 81-84 (2001).

Gamboa-Bobadilla, G.M., "Implant Breast Reconstruction using Acellular Dermal Matrix", Annals of Plastic Surgery, 56(1): 22-25 (2006).

Salzberg, C.A., "Nonexpansive Immediate Breast Reconstruction using Human Acellular Tissue Matrix Graft (AlloDerm)", Annals of Plastic Surgery, 57(1): 1-5 (2006).

Topol, B.M. et al., "Immediate Single-Stage Breast Reconstruction using Implants and Human Acellular Dermal Tissue Matrix With Adjustment of the Lower Pole of the Breast to Reduce Unwanted Lift", Annals of Plastic Surgery, 61(5): 494-499 (2008).

Zienowicz, R.J. et al., "Implant-Based Breast Reconstruction With Allograft", Plast. Reconstr. Surg., 120: 373-374 (2007).

International Search Report and Written Opinion for PCT/US2010/042575, dated Jan. 14, 2011.

(56) References Cited

OTHER PUBLICATIONS

U.S. Appl. No. 12/506,839, filed Jul. 21, 2009, now U.S. Pat. No. 8,986,377.
Musculoskeletal Transplant Foundation, Flex HD Max, 2016.
Musculoskeletal Transplant Foundation, Flex HD Instructions, 2012.
Musouloskeletal Transplant Foundation, Flex HD, 2012.
Non-Final Rejection for corresponding U.S. Appl. No. 15/680,666, dated Jun. 22, 2018.
Chinese First Office Action corresponding to CN201510397303.6, dated Sep. 9, 2016.

\* cited by examiner

GRAFT MATERIALS FOR SURGICAL BREAST PROCEDURES

This application is a continuation application that claims the benefit of a non-provisional patent application entitled "Graft Materials For Surgical Breast Procedures", which was filed on Jul. 21, 2009, and assigned Ser. No. 12/506,839, now U.S. Pat. No. 8,986,377. The entire content of the foregoing non-provisional application is incorporated herein by reference.

The present disclosure relates to graft materials for surgical breast or other plastic surgery procedures.

BACKGROUND

Graft materials can be used in a wide range of surgical procedures to augment tissue or repair or correct tissue defects. One application of graft materials is the field of cosmetic and reconstructive surgical breast procedures, a field in which the number of procedures performed each year continues to increase. Some graft materials are typically provided to surgeons as a sheet or sheet-like material, which the surgeon can cut to the desired size and shape before implantation. Graft materials can be very expensive and can pose challenges for attaining adequate conformance to underlying features of the implantation site.

Accordingly, there is a need for improved graft materials.

SUMMARY

According to certain embodiments, a graft material for surgical breast procedures is disclosed that includes a sample of biocompatible material with a first edge and a second edge. The first edge has a convex portion that curves away from the second edge, and the second edge has a convex portion that curves away from the first edge.

According to certain embodiments, a graft material for surgical breast procedures is disclosed that includes a sample of biocompatible material with a set of perforations that form an arcuate pattern across at least a portion of the sample of biocompatible material.

According to certain embodiments, a method of making one or more graft devices is disclosed. The method includes cutting one or more samples from a sheet of biocompatible material such that the samples are sized and shaped for conforming to a portion of a surface of a breast implant.

DESCRIPTION OF CERTAIN EXEMPLARY EMBODIMENTS

Figure 1:
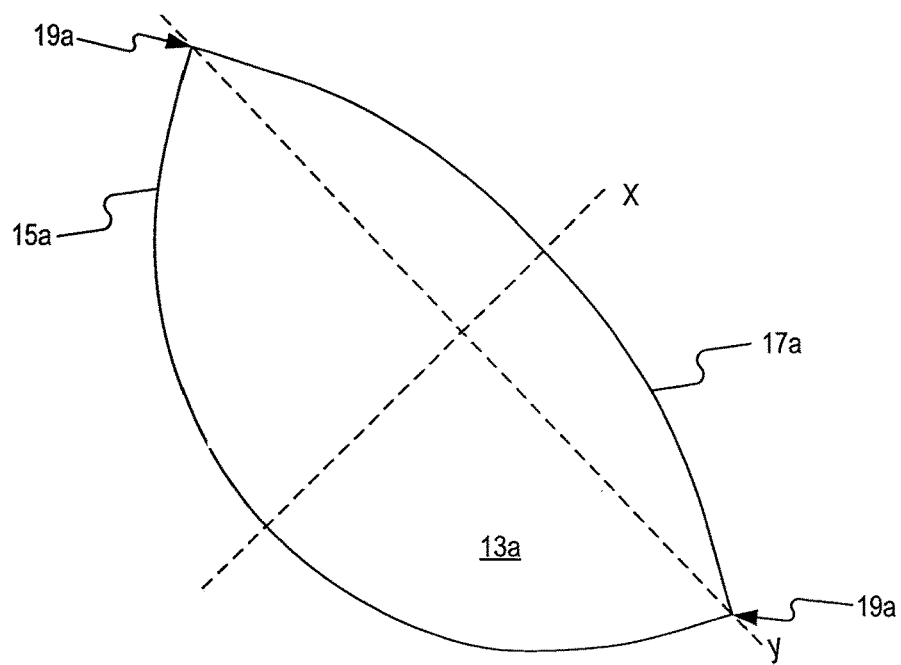
FIG. 1 is a perspective view of one exemplary embodiment of a graft material.

Reference will now be made in detail to the present embodiments (exemplary embodiments) of the invention, examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including," as well as other forms, such as "includes" and "included," is not limiting. Also, terms such as "element" or "component" encompass both elements and components comprising one unit and elements and components that comprise more than one subunit, unless specifically stated otherwise. Also, the use of the term "portion" may include part of a moiety or the entire moiety.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose.

The term "graft material," as used herein, generally refers to a material such as, for example, tissue, processed tissue, or synthetics that can be attached to or inserted into a bodily part.

The terms "sheet" and "sheet-like," as used herein, generally refer to a broad, relatively thin, surface or layer of a material. Such sheets can, but may not, be relatively flexible, and may be flat or uniform in thickness or may vary in thickness across their surface.

The terms "breast implant" and "implant," as used herein, generally refer to medical devices that are implanted either under breast tissue or under the chest muscle for breast augmentation or reconstruction. Such implants can include saline filled or silicone gel implants, or other implants that provide volume for breast augmentation.

The present disclosure relates to graft materials and methods of using graft materials in breast or other plastic surgery procedures. The graft materials can be used for tissue augmentation, repair or regeneration of damaged tissue, and/or correction of tissue defects. As such, the graft material and methods discussed herein may be suitable for a wide range of surgical applications. In various embodiments, the graft materials and methods discussed herein may be suitable for various types of surgical breast procedures, such as, for example, aesthetic surgery associated with mastectomy or lumpectomy, breast reconstruction, breast augmentation, breast enhancement, breast reduction, mastopexy, and revisionary breast surgeries.

Various embodiments of graft materials discussed herein include a sample of biocompatible material. In some embodiments, a sample of biocompatible material may be a flat sheet or sheet-like in form. A sample of biocompatible material may be a single layer or may be multi-layered. In some embodiments, a sample of biocompatible material may be a material that facilitates revascularization and cell repopulation. For example, as further described below, certain embodiments can include an acellular tissue matrix ("ATM").

FIG. 1 provides a perspective view of one exemplary embodiment of a graft material for surgical breast procedures. The graft material may comprise a sample of biocompatible material 13a. Sample of biocompatible material 13a can have a first edge 15a and a second edge 17a. A portion of first edge 15a can be convex, curving away from second edge 17a. Similarly, a portion of second edge 17a can be convex, curving away from first edge 15a. As depicted in FIG. 1, first edge 15a and second edge 17a may both be substantially convex, thus making sample of biocompatible material 13a generally biconvex in shape.

In one exemplary embodiment, either or both first edge 15a and second edge 17a may be substantially parabolically curved. As such, the curvature of each may be characterized, in part, by the distance from the focus to the vertex of each parabola. For example, as depicted in FIG. 1, first edge 15a and second edge 17a may be substantially parabolically curved, with the parabolic curve of second edge 17a having a greater distance from its focus to its vertex than that of first edge 15a. Furthermore, in certain embodiments, sample of biocompatible material 13a may be implanted across breast tissue of a patient such that first edge 15a is positioned lateral and inferior to first edge 17a, and such that a longitudinal axis y of sample of biocompatible material 13a is at about a 45° angle with respect to the transverse plane of the patient.

Figure 2:
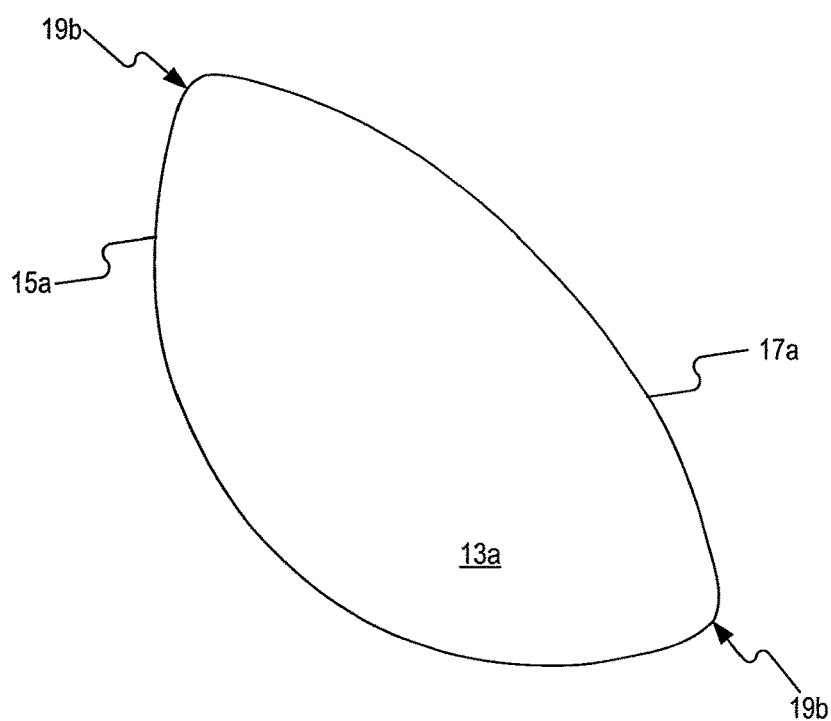
FIG. 2 is a perspective view of one exemplary embodiment of a graft material.
Figure 3:
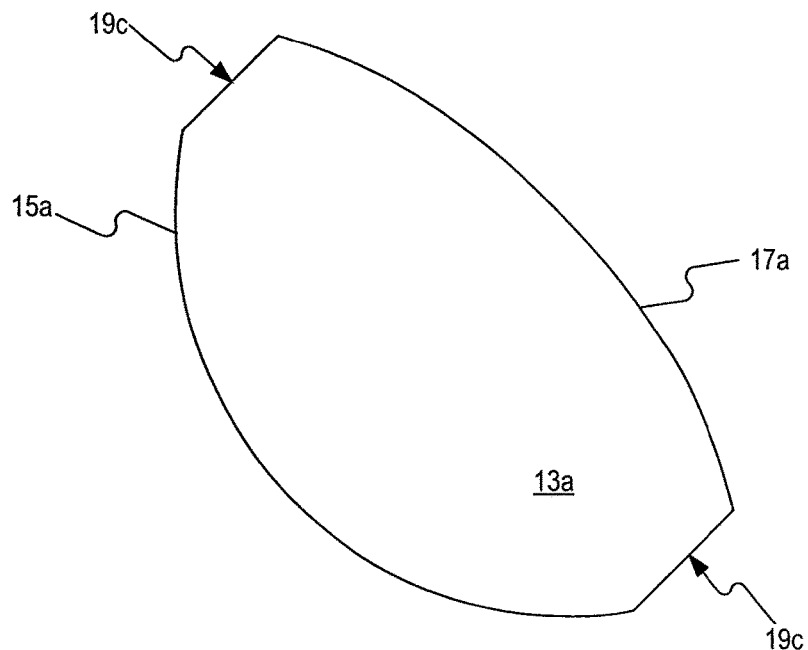
FIG. 3 is a perspective view of one exemplary embodiment of a graft material.

First edge 15a and second edge 17a may join at an apex. Depending on the needs of the procedure, the apex can be configured in numerous shapes, such as, for example, a pointed apex 19a, as depicted in FIG. 1, a rounded apex 19b, as depicted in FIG. 2, or a squared apex 19c, as depicted in FIG. 3. Further, first edge 15a and second edge 17a may be joined at more than one apex, and each apex may be shaped differently. Similarly, sample of biocompatible material 13a may be symmetrical, for example about an axis x, as depicted in FIG. 1, or asymmetrical, such as 13b depicted in FIG. 4.

Figure 4:
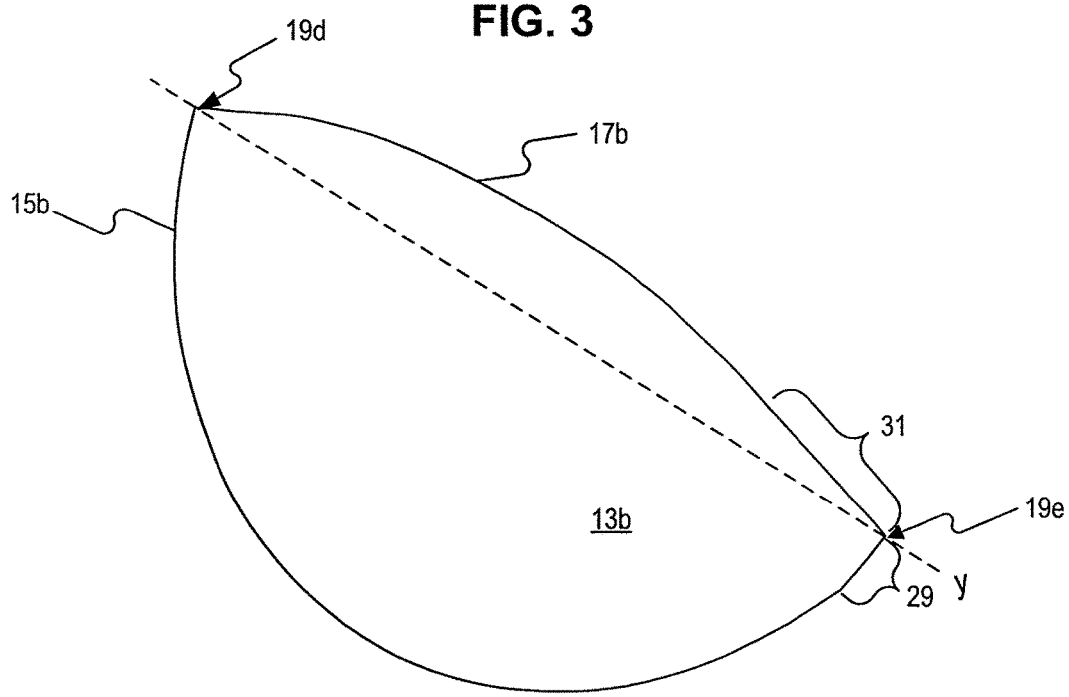
FIG. 4 is a perspective view of one exemplary embodiment of a graft material.

In some exemplary embodiments, the edges of a sample of biocompatible material may have multiple portions with varying degrees of curvature, including, for example, nonconvex, straight, or concave portions, in addition to a convex portion. For example, as shown in FIG. 4, a sample of biocompatible material 13b may have a first edge 15b and a second edge 17b joined at a first apex 19d and a second apex 19e. First edge 15b may have a nonconvex portion 29, and second edge 17b may have a nonconvex portion 31. The nonconvex portions of first edge 15b and second edge 17b may converge at the second apex 19e. In certain embodiments, sample of biocompatible material 13b may be implanted across breast tissue of a patient such that second apex 19e is positioned medial and inferior to first apex 19d, and such that a longitudinal axis y of sample of biocompatible material 13b is at about a 45° angle with respect to the transverse plane of the patient. Further, in some embodiments, the nonconvex portions of first edge 15b and second edge 17b may be substantially straight.

Since graft materials may be provided in sheet or sheet-like forms, and the underlying features of the implantation site are often rounded or irregularly shaped, it may be difficult to attain adequate conformance between the graft material and the underlying features. This can be challenging in surgical breast procedures, where the desired outcome involves unique aesthetic and structural demands. Specifically, it can be difficult to avoid undesired pleating after implanting a sheet of graft material over a rounded breast mound and/or breast implant. In some circumstances, pleating may be undesirable because it may be perceptible by palpation and/or it may negatively affect cell integration or infiltration. Providing adequate support to maintain breast shape and projection and to minimize or avoid eventual ptosis, or sagging, of the breast can also be a challenge. In some embodiments, graft materials incorporating edge configurations, as described herein, may improve surface coverage and conformance to underlying anatomical features when implanted in a patient.

Figure 5:
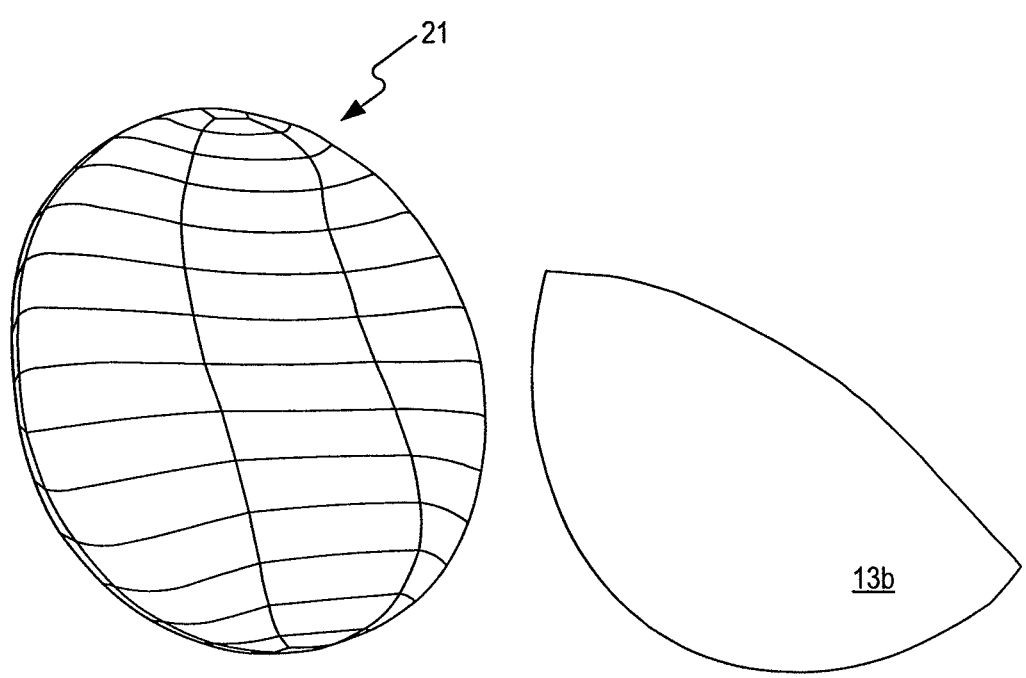
FIG. 5 is a perspective view of one exemplary embodiment of a graft material, illustrated in relation to a breast implant.

In some exemplary embodiments, sample of biocompatible material 13b may be specifically sized and shaped to conform to a portion of a surface of a breast implant. For example, a specific size and shape may be derived by modeling the lower pole of a breast implant in its proper orientation with respect to gravity. Accordingly, FIG. 5 shows a modeled Style 410 Anatomical Implant (Allergan, Inc. (Santa Barbara, Calif.)) 21 in a vertical orientation and a sample of biocompatible material 13b having a shape produced by modeling biocompatible material covering 50% of implant 21 such that sample of biocompatible material 13b may be bordered by the inframammary fold, the lateral fold, and the inferior edge of the pectoralis major muscle when implanted in a patient. In some embodiments, tailoring the size and shape of the graft material to a breast implant can provide better conformance of the graft material to the implant and/or surrounding tissue and may reduce the frequency of pleating.

Currently, graft material is typically provided to surgeons as sheets or sheet-like devices, and the surgeon may cut the material to the desired size and shape before implantation. While providing flexibility to surgeons, this practice has several drawbacks. Often, substantial amounts of the graft material can be wasted. For example, surgeons may inaccurately estimate the size of the device needed, either overestimating and disposing of the unused portion of an unnecessarily large device, or underestimating and necessitating the opening of a second packaged device. Such waste can add substantial costs to procedures, as graft materials are often very expensive and may be priced based on the amount of material included. Furthermore, it may be difficult for surgeons to accurately cut the material freehand into a specific optimum shape.

Figure 6:
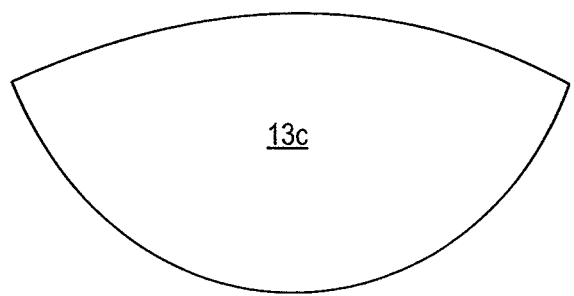
FIG. 6 is a perspective view of one exemplary embodiment of a graft material.
Figure 7:
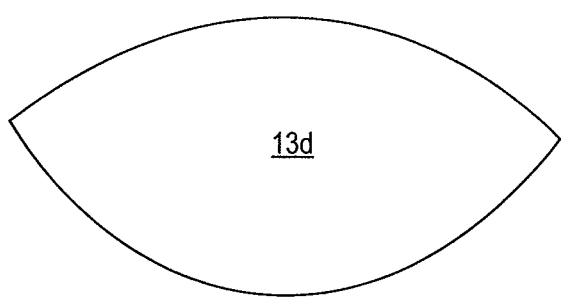
FIG. 7 is a perspective view of one exemplary embodiment of a graft material.

In some embodiments, ready-to-use, off-the-shelf graft materials can be made that are designed to conform to breast implants of various specifications. For example, in some embodiments, a sample of biocompatible material can be specifically sized and shaped to conform to a particular type of breast implant, such as, for example, gel or saline, round or anatomical/contour, form-stable or nonform-stable, and smooth or textured implants. Alternatively or additionally, a sample of biocompatible material can be specifically sized and shaped to conform to breast implants of a predetermined volume. For example, graft materials can be made from a sample of biocompatible material sized and shaped specifically for common breast implant volumes, such as, between about 400 and about 550 cubic centimeters, between about 250 and about 400 cubic centimeters, between about 250 and about 550 cubic centimeters, or less than about 250 cubic centimeters. Further, a sample of biocompatible material can be specifically shaped to conform to breast implants of a particular profile, such as, for example, samples of biocompatible material 13c and 13d, as shown in FIGS. 6 and 7. Sample of biocompatible material 13c may be better suited for a moderate profile implant while sample of biocompatible material 13d may be better suited for a high profile implant. Providing graft materials specifically sized and shaped for breast implants of particular specifications (e.g., volume, surface area, surface texture, material, profile, mechanical properties) may remove some of the uncertainty associated with a surgeon attempting to estimate the optimal size and shape of graft material needed for a particular surgery. This in turn, may reduce the amount of graft material that is sometimes wasted due to inaccurate estimates. This may also reduce the need to perform trimming/resizing of the graft material during surgery. Avoiding trimming/resizing during surgery may reduce the duration of the surgery, which can be beneficial both for the health of the patient and for reducing the cost of the surgery.

In other exemplary embodiments, the sample of biocompatible material can be slightly oversized relative to the modeled size and shape. Slight oversizing can allow the graft material to accommodate breast implants of different profiles. Additionally, an identified size and shape can be slightly oversized in some portions to make the graft material generally symmetrical, such as, for example, sample of biocompatible material 13a. While this may result in small excesses in material use, this could aid the surgeon by making it unnecessary to identify a particular side that must be positioned medially or laterally.

In some embodiments, the graft material described herein can be used to assist in treating patients in whom complications related to breast implants have arisen. Such complications can include malposition (e.g., inframammary fold malposition, lateral malposition, symmastia), stretch deformity, coverage issues (e.g., wrinkling and rippling), and capsular contraction. For example, in some embodiments, the graft material described herein may be used to help control the breast pocket size and location, act as an "internal bra" to hold the implant in place, support fold repairs, support the implant to reduce the pressure and tension on patient's own tissue, and/or provide an additional layer for coverage of the implant.

Figure 8:
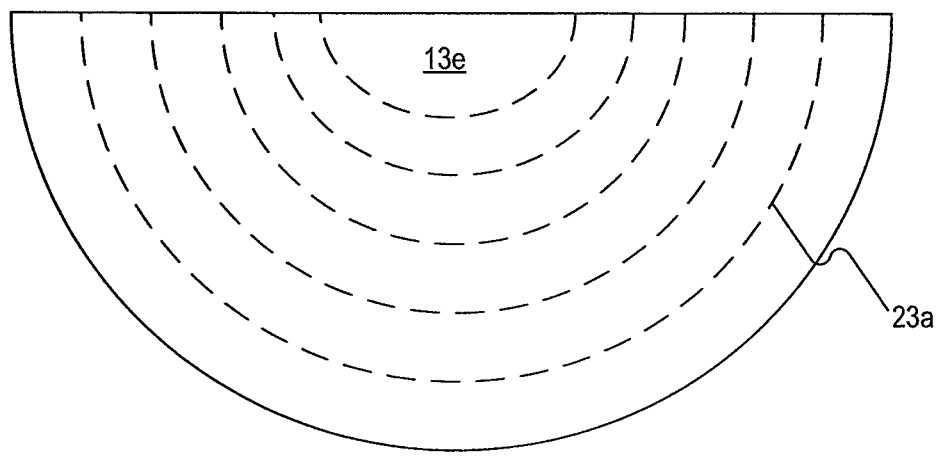
FIG. 8 is a perspective view of one exemplary embodiment of a graft material.

Exemplary embodiments may further include one or more sets of perforations across at least a portion of the sample of biocompatible material. Perforations can be formed in the sample of biocompatible material by any suitable method, such as, for example, die cutting, laser drilling, water jet cutting, skin graft meshing, or manual incision (e.g., with a scalpel). In some exemplary embodiments, such a set of perforations can be used to improve the conformance of a sample of biocompatible material to anatomical structures and/or a breast implant. For example, as depicted in FIG. 8, set of perforations 23a may form an arcuate pattern across sample of biocompatible material 13e. In some exemplary embodiments, the arcuate pattern can improve conformance of graft materials to rounded structures, such as, for example, breast tissue. In certain embodiments, set of perforations 23a may create a mesh pattern that enables separation and/or expansion of portions of biocompatible material 13e such that portions of biocompatible material 13e may be capable of covering larger surface areas. In some exemplary embodiments, one or more sets of perforations across at least a portion of the sample of biocompatible material may also be used to modify the mechanical properties of the sample of biocompatible and/or affect tissue ingrowth.

Figure 9:
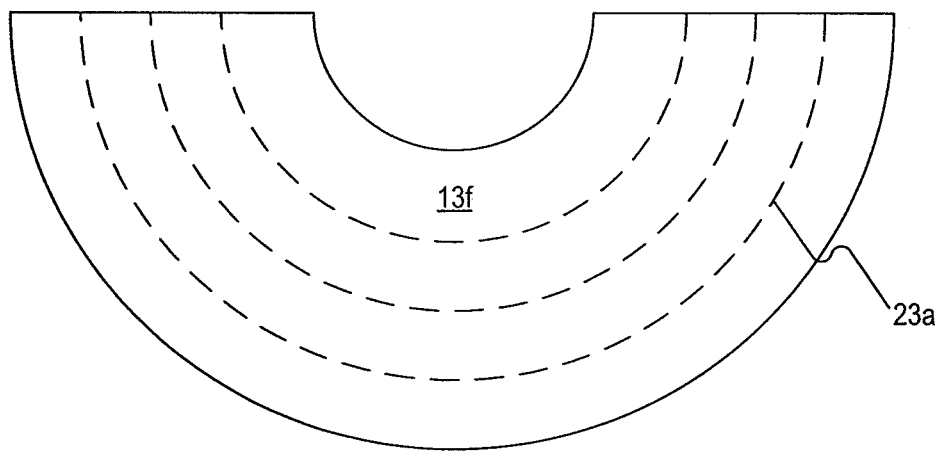
FIG. 9 is a perspective view of one exemplary embodiment of a graft material.
Figure 10:
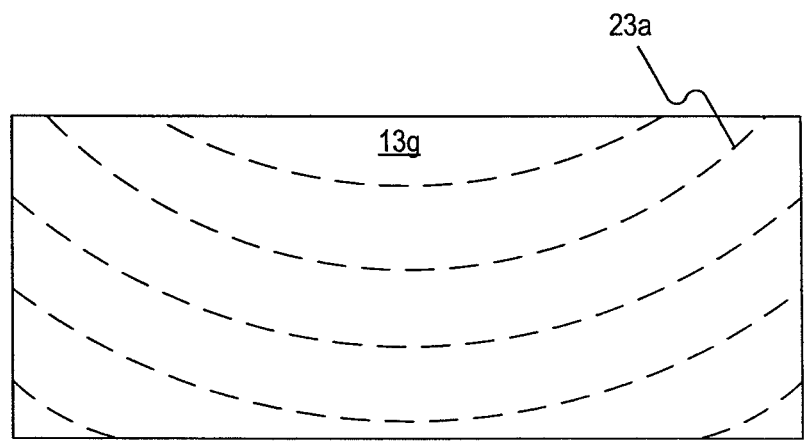
FIG. 10 is a perspective view of one exemplary embodiment of a graft material.
Figure 11:
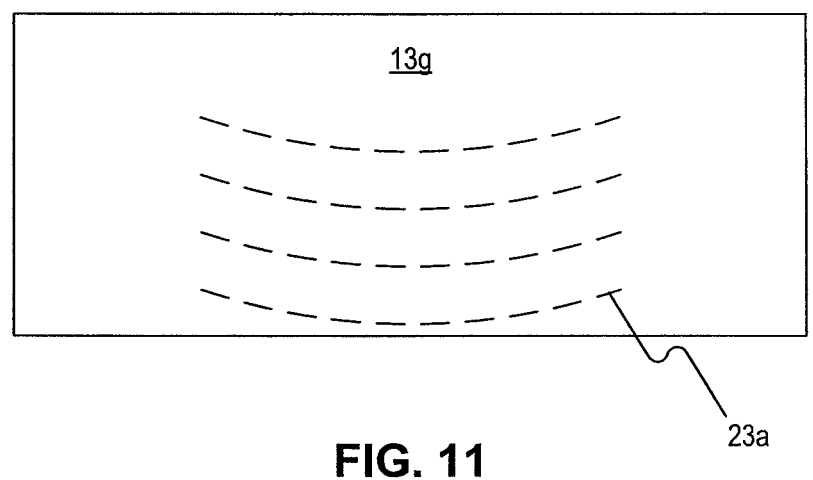
FIG. 11 is a perspective view of one exemplary embodiment of a graft material.
Figure 12:
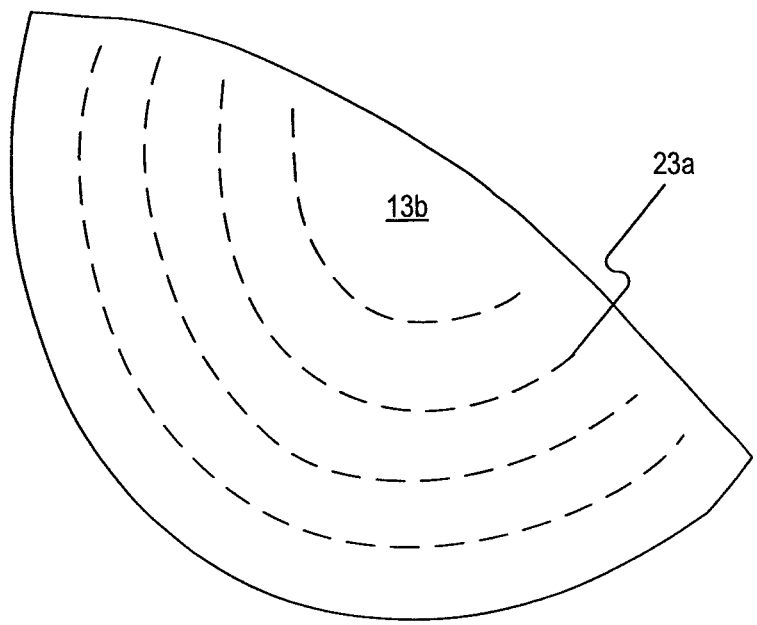
FIG. 12 is a perspective view of one exemplary embodiment of a graft material.
Figure 13:
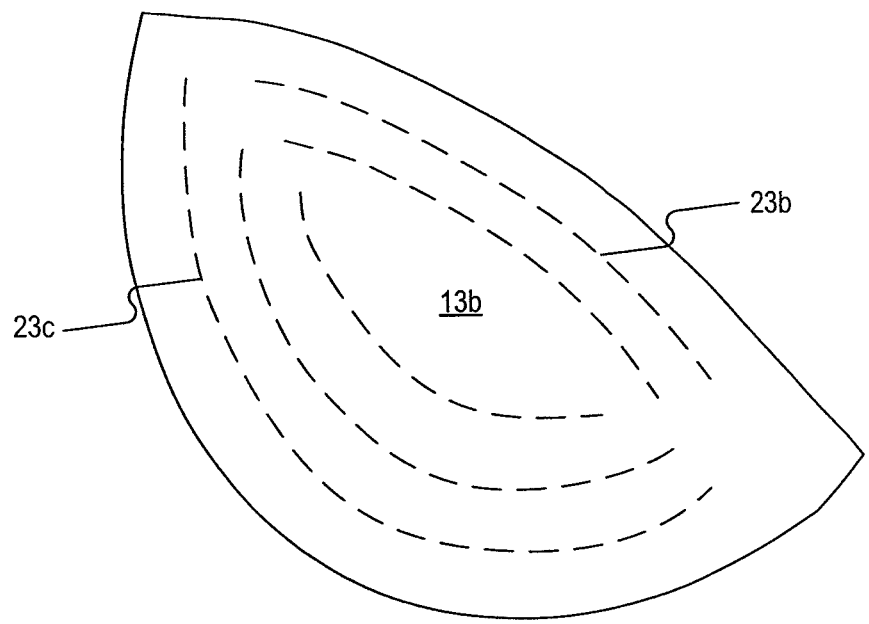
FIG. 13 is a perspective view of one exemplary embodiment of a graft material.

In various embodiments, one or more sets of perforations can be incorporated into graft material in numerous configurations depending on the structure of the tissue on which the graft material is to be implanted or type of breast implant being used. For example, a set of perforations 23a can be included on samples of biocompatible material of any desired shape, such as, for example, semicircular (13e, 13f) (including semicircular with a portion removed, as depicted in FIG. 9, to accommodate an anatomical feature, such as, for example, the nipple-areola complex), rectangular (13g), or customized to a breast implant (13b), as described above in greater detail. The set of perforations may be uniform or irregular in shape and spacing. A set of perforations may include individual perforations that are arcuate, individual perforations that are straight but arranged in an arcuate pattern, or a combination of both, depending on the features of the implantation surface. Individual perforations can be formed as slits, circular apertures, or any other shape. Furthermore, set of perforations 23a can be placed across an entire surface of biocompatible material 13g, as depicted in FIG. 10, or simply a portion of a surface of biocompatible material 13g, as depicted in FIG. 11, in order to achieve desired conformance characteristics across different portions of the sample of biocompatible material 13g. Similarly, as depicted in FIG. 13, multiple sets of perforations 23b, 23c can be included on a single sample of biocompatible material to attain a desired variation of conformance characteristics across the sample of biocompatible material.

Figure 14:
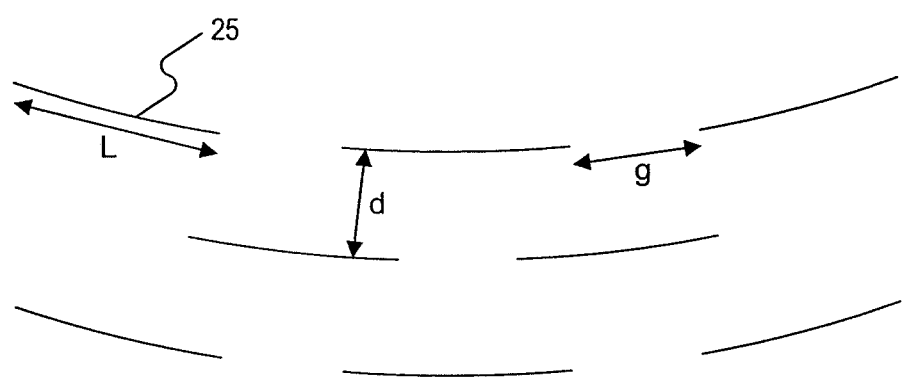
FIG. 14 is a detailed view of a set of perforations consistent with one exemplary embodiment of a graft material.

In some exemplary embodiments, as depicted in FIG. 14, a uniform set of perforations may include a series of parallel slits 25. Each slit 25 may have a generally uniform length L, adjacent slits may be separated longitudinally by a generally uniform gap distance g, and adjacent parallel slits may be separated by a generally uniform horizontal separation distance d. In some exemplary embodiments, length L may be between about 0.1 and about 20 millimeters, gap distance g may be between about 0.1 and about 20 millimeters, and horizontal separation distance d may be between about 0.1 and about 20 millimeters. Further, in some exemplary embodiments, length L may be between about 4 and about 8 millimeters, gap distance g may be between about 2 and about 6 millimeters, and horizontal separation distance d may be between about 2 and about 6 millimeters. In some exemplary embodiments, adjacent parallel slits may be offset longitudinally with respect to each other as depicted in FIG. 14. Such a configuration of a set of parallel slits may provide improved conformance to a sample of biocompatible material while still maintaining sufficient support strength.

In some embodiments, the samples of biocompatible material can comprise any suitable synthetic or biologic material, such as, for example, medical-grade silicon, autologous or cadaveric tissue, and/or biomatrices, such as, for example, ATM.

As used herein, ATM refers to a tissue-derived biomatrix structure that can be made from any of a wide range of collagen-containing tissues by removing all, or substantially all, viable cells and all detectable subcellular components and/or debris generated by killing cells. As used herein, an ATM lacking "substantially all viable cells" is an ATM in which the concentration of viable cells is less than 1% (e.g., less than: 0.1%; 0.01%; 0.001%; 0.0001%; 0.00001%; or 0.000001%) of that in the tissue or organ from which the ATM was made.

ATM's that are suitable for use in the present disclosure include those that contain, lack, or substantially lack, an epithelial basement membrane. As used herein, an ATM that "substantially lacks" an epithelial basement membrane is an acellular tissue matrix containing less than 5% (e.g., less than: 3%; 2%; 1%; 0.5%; 0.25%; 0.1%; 0.01%; 0.001%; or even less than 0.0001%) of the epithelial basement membrane possessed by the corresponding unprocessed tissue from which the acellular tissue matrix was derived.

An epithelial basement membrane is a thin sheet of extracellular material contiguous with the basilar aspect of epithelial cells. Sheets of aggregated epithelial cells form an epithelium. Thus, for example, the epithelium of skin is called the epidermis, and the skin epithelial basement membrane lies between the epidermis and the dermis. The epithelial basement membrane is a specialized extracellular matrix that provides a barrier function and an attachment surface for epithelial-like cells; however, it does not contribute any significant structural or biomechanical role to the underlying tissue (e.g., dermis). Components of epithelial basement membranes include, for example, laminin, collagen type VII, and nidogen. The temporal and spatial organizations of the epithelial basement membrane distinguish it from, e.g., the dermal extracellular matrix.

Accordingly, in some non-limiting embodiments, the ATMs suitable for use in the present disclosure contain epithelial basement membrane. In other non-limiting embodiments, ATM may lack or substantially lack epithelial basement membrane.

ATM's suitable for use in the present disclosure may, for example, retain certain biological functions, such as cell recognition, cell binding, the ability to support cell spreading, cell proliferation, cellular in-growth and cell differentiation. Such functions may be provided, for example, by undenatured collagenous proteins (e.g., type I collagen) and a variety of non-collagenous molecules (e.g., proteins that serve as ligands for either molecules such as integrin receptors, molecules with high charge density such as glycosaminoglycans (e.g., hyaluronan) or proteoglycans, or other adhesins). In some embodiments, the ATM's may retain certain structural functions, including maintenance of histological architecture and maintenance of the three-dimensional array of the tissue's components. The ATM's described herein may also, for example, exhibit desirable physical characteristics such as strength, elasticity, and durability, defined porosity, and retention of macromolecules.

ATMs suitable for use in the present disclosure may be crosslinked or uncrosslinked.

The efficiency of the biological functions of an ATM can be measured, for example, by the ability of the ATM to support cell proliferation. In some embodiments of the present disclosure, the ATM exhibits at least 50% (e.g., at least: 50%; 60%; 70%; 80%; 90%; 95%; 98%; 99%; 99.5%; 100%; or more than 100%) of that of the native tissue or organ from which the ATM is made.

In some embodiments, the graft material is amenable to being remodeled by infiltrating cells such as differentiated cells of the relevant host tissue, stem cells such as mesenchymal stem cells, or progenitor cells. This may be accomplished, for example, by forming the grafted matrix material from tissue that is identical to the surrounding host tissue, but such identity is not necessary.

Remodeling may be directed by the above-described ATM components and signals from the surrounding host tissue (such as cytokines, extracellular matrix components, biomechanical stimuli, and bioelectrical stimuli). For example, the presence of mesenchymal stem cells in the bone marrow and the peripheral circulation has been documented in the literature and shown to regenerate a variety of musculoskeletal tissues [Caplan (1991) J. Orthop. Res. 9:641-650; Caplan (1994) Clin. Plast. Surg. 21:429-435; and Caplan et al. (1997) Clin Orthop. 342:254-269]. Additionally, the graft must provide some degree (greater than threshold) of tensile and biomechanical strength during the remodeling process.

ATM in accordance with the present disclosure may be manufactured from a variety of source tissues. For example, ATM may be produced from any collagen-containing soft tissue and muscular skeleton (e.g., dermis, fascia, pericardium, dura, umbilical cords, placentae, cardiac valves, ligaments, tendons, vascular tissue (arteries and veins such as saphenous veins), neural connective tissue, urinary bladder tissue, ureter tissue, or intestinal tissue), as long as the above-described properties are retained by the matrix. Moreover, the tissues in which ATM graft material are placed may include any tissue that can be remodeled by invading or infiltrating cells. Non-limiting examples of such tissues include skeletal tissues such as bone, cartilage, ligaments, fascia, and tendon. Other tissues in which any of the above grafts can be placed include, for example, skin, gingiva, dura, myocardium, vascular tissue, neural tissue, striated muscle, smooth muscle, bladder wall, ureter tissue, intestine, and urethra tissue.

While an ATM may be made from one or more individuals of the same species as the recipient of the ATM graft, this is not necessarily the case. Thus, for example, an ATM may be made from porcine tissue and implanted in a human patient. Species that can serve as recipients of ATM and donors of tissues or organs for the production of the ATM include, without limitation, humans, nonhuman primates (e.g., monkeys, baboons, or chimpanzees), porcine, bovine, horses, goats, sheep, dogs, cats, rabbits, guinea pigs, gerbils, hamsters, rats, or mice. Of particular interest as donors are animals (e.g., pigs) that have been genetically engineered to lack the terminal α-galactose moiety. For descriptions of appropriate animals see co-pending U.S. application Ser. No. 10/896,594 and U.S. Pat. No. 6,166,288, the disclosures of all of which are incorporated herein by reference in their entirety.

As an example of suitable porcine-derived tissue, non-limiting mention is made of STRATTICE™, which is a porcine dermal tissue produced by Lifecell Corporation (Branchburg, N.J.). The tissue matrix may be derived from porcine skin by removing the epidermis while leaving the dermal matrix substantially intact. In some embodiments, the porcine-derived tissue matrix may facilitate tissue ingrowth and remodeling with the patient's own cells. In other embodiments, the material can include a collagenous matrix derived from human cadaver skin (e.g. ALLODERM®, Lifecell Corporation (Branchburg, N.J.)) that has been processed to remove both the epidermis and cells.

In some embodiments of the present disclosure, a freeze dried ATM is produced from human dermis by the LifeCell Corporation (Branchburg, N.J.) and marketed in the form of small sheets as ALLODERM®. Such sheets are marketed by the LifeCell Corporation as rectangular sheets with the dimensions of, for example, 1 cm×2 cm, 3 cm×7 cm, 4 cm×8 cm, 5 cm×10 cm, 4 cm×12 cm, and 6 cm×12 cm. The cryoprotectant used for freezing and drying ALLODERM® is a solution of 35% maltodextrin and 10 mM ethylenediaminetetraacetate (EDTA). Thus, the final dried product contains about 60% by weight ATM and about 40% by weight maltodextrin. The LifeCell Corporation also makes an analogous product made from porcine dermis (designated XENODERM) having the same proportions of ATM and maltodextrin as ALLODERM®.

As an alternative to using such genetically engineered animals as donors, appropriate tissues and organs can be treated, before or after decellularization, with the enzyme α-galactosidase, which removes terminal α-galactose (α-gal) moieties from saccharide chains on, for example, glycoproteins. Methods of treating tissue with α-galactosidase to remove these moieties are described in, for example, U.S. Pat. No. 6,331,319, the disclosure of which is incorporated herein by reference in its entirety.

In an implementation, either before or after the soft tissue cells are killed in the ATM, the collagen-containing material is subjected to in vitro digestion of the collagen-containing material with one or more glycosidases, and particularly galactosidases, such as α-galactosidase. In particular, α-gal epitopes are eliminated by enzymatic treatment with α-galactosidases.

The N-acetylactosamine residues are epitopes that are normally expressed on human and mammalian cells and thus are not immunogenic. The in vitro digestion of the collagen-containing material with glycosidases may be accomplished by various methods. For example, the collagen-containing material can be soaked or incubated in a buffer solution containing glycosidase. Alternatively, a buffer solution containing the glycosidase can be forced under pressure into the collagen-containing material via a pulsatile lavage process.

Elimination of the α-gal epitopes from the collagen-containing material may diminish the immune response against the collagen-containing material. The α-gal epitope is expressed in non-primate mammals and in New World monkeys (monkeys of South America) as $1 \times 10^6$-$35 \times 10^6$ epitopes per cell, as well as on macromolecules such as proteoglycans of the extracellular components. U. Galili et al., J. Biol. Chem. 263: 17755 (1988). This epitope is absent in Old World primates (monkeys of Asia and Africa and apes) and humans, however. Id. Anti-gal antibodies are produced in humans and primates as a result of an immune response to α-gal epitope carbohydrate structures on gastrointestinal bacteria. U. Galili et al., Infect. Immun. 56: 1730 (1988); R. M. Hamadeh et al., J. Clin. Invest. 89: 1223 (1992).

Since non-primate mammals (e.g., pigs) produce α-gal epitopes, xenotransplantation by injection of collagen-containing material from these mammals into primates often results in rejection because of primate anti-Gal binding to these epitopes on the collagen-containing material. The binding results in the destruction of the collagen-containing material by complement fixation and by antibody dependent cell cytotoxicity. U. Galili et al., Immunology Today 14: 480 (1993); M. Sandrin et al., Proc. Natl. Acad. Sci. USA 90: 11391 (1993); H. Good et al., Transplant. Proc. 24: 559 (1992); B. H. Collins et al., J. Immunol. 154: 5500 (1995). Furthermore, xenotransplantation results in major activation of the immune system to produce increased amounts of high affinity anti-gal antibodies. Accordingly, the substantial elimination of α-gal epitopes from cells and from extracellular components of the collagen-containing material, and the prevention of reexpression of cellular α-gal epitopes can diminish the immune response against the collagen-containing material associated with anti-gal antibody binding to α-gal epitopes.

ATMs suitable for use in the present disclosure may be provided in various forms depending on the tissue or organ from which it is derived, the nature of the recipient tissue or organ, and the nature of the damage or defect in the recipient tissue or organ. Thus, for example, a ATM derived from a heart valve can be provided as a whole valve, as small sheets or strips, or as pieces cut into any of a variety of shapes and/or sizes. The same concept applies to ATM produced from any of the above-listed tissues and organs. In some embodiments, the ATM is made from a recipient's own collagen-based tissue.

ATM's suitable for use in the present disclosure can be produced by a variety of methods, so long as their production results in matrices with the above-described biological and structural properties. As non-limiting examples of such production methods, mention is made of the methods described in U.S. Pat. Nos. 4,865,871; 5,366,616, and 6,933,326, U.S. patent application Publication Nos. US 2003/0035843 A1, and US 2005/0028228 A1, all of which are incorporated herein by reference in their entirety.

In general, the steps involved in the production of an ATM include harvesting the tissue from a donor (e.g., a human cadaver or any of the above-listed mammals), chemical treatment so as to stabilize the tissue and avoid biochemical and structural degradation together with, or followed by, cell removal under conditions which similarly preserve biological and structural function. After thorough removal of dead and/or lysed cell components that may cause inflammation as well as any bioincompatible cell-removal agents, the matrix can be treated with a cryopreservation agent and cryopreserved and, optionally, freeze dried, again under conditions necessary to maintain the described biological and structural properties of the matrix. After freeze drying, the tissue can, optionally, be pulverized or micronized to produce a particulate ATM under similar function-preserving conditions. After cryopreservation or freeze-drying (and optionally pulverization or micronization), the ATM can be thawed or rehydrated, respectively. All steps are generally carried out under aseptic, preferably sterile, conditions.

The initial stabilizing solution arrests and prevents osmotic, hypoxic, autolytic, and proteolytic degradation, protects against microbial contamination, and reduces mechanical damage that can occur with tissues that contain, for example, smooth muscle components (e.g., blood vessels). The stabilizing solution may contain an appropriate buffer, one or more antioxidants, one or more oncotic agents, one or more antibiotics, one or more protease inhibitors, and in some cases, a smooth muscle relaxant.

The tissue is then placed in a processing solution to remove viable cells (e.g., epithelial cells, endothelial cells, smooth muscle cells, and fibroblasts) from the structural matrix without damaging the basement membrane complex or the biological and structural integrity of the collagen matrix. The processing solution may contain an appropriate buffer, salt, an antibiotic, one or more detergents (e.g., Triton-x-100, sodium deoxycholate, polyoxyethylene (20) sorbitan mono-oleate), one or more agents to prevent cross-linking, one or more protease inhibitors, and/or one or more enzymes. The tissue is then treated with a processing solution containing active agents, and for a time period such that the structural integrity of the matrix is maintained.

Alternatively, the tissue can be cryopreserved prior to undergoing water replacement. If so, after decellularization, the tissue is incubated in a cryopreservation solution. This solution may contain at least one cryoprotectant to minimize ice crystal damage to the structural matrix that could occur during freezing. If the tissue is to be freeze dried, the solution may also contain at least one dry-protective components, to minimize structural damage during drying and may include a combination of an organic solvent and water which undergoes neither expansion nor contraction during freezing. The cryoprotective and dry-protective agents may be the same. If the tissue is not going to be freeze dried, it can be frozen by placing it (in a sterilized container) in a freezer at about −80° C., or by plunging it into sterile liquid nitrogen, and then storing at a temperature below −160° C. until use. The tissue sample can be thawed prior to use by, for example, immersing a sterile non-permeable vessel (see below) containing the sample in a water bath at about 37° C. or by allowing the tissue to come to room temperature under ambient conditions.

If the tissue is to be frozen and freeze dried, following incubation in the cryopreservation solution, the tissue may be packaged inside a sterile vessel that is permeable to water vapor yet impermeable to bacteria, e.g., a water vapor permeable pouch or glass vial. As a non-limiting example, one side of the pouch may include medical grade porous TYVEK® membrane, a trademarked product of DuPont Company of Wilmington, Del. This membrane is porous to water vapor and impervious to bacteria and dust. The TYVEK® membrane is heat sealed to an impermeable polyethylene laminate sheet, leaving one side open, thus forming a two-sided pouch. The open pouch is sterilized by irradiation prior to use. The tissue is aseptically placed (through the open side) into the sterile pouch. The open side is then aseptically heat sealed to close the pouch. The packaged tissue is henceforth protected from microbial contamination throughout subsequent processing steps.

The vessel containing the tissue is cooled to a low temperature at a specified rate which is compatible with the specific cryoprotectant formulation to minimize the freezing damage. See U.S. Pat. No. 5,336,616 for non-limiting examples of appropriate cooling protocols. The tissue is then dried at a low temperature under vacuum conditions, such that water vapor is removed sequentially from each ice crystal phase.

At the completion of the drying of the samples in the water vapor permeable vessel, the vacuum of the freeze drying apparatus is reversed with a dry inert gas such as nitrogen, helium or argon. While being maintained in the same gaseous environment, the semipermeable vessel is placed inside an impervious (i.e., impermeable to water vapor as well as microorganisms) vessel (e.g., a pouch) which is further sealed, e.g., by heat and/or pressure. Where the tissue sample was frozen and dried in a glass vial, the vial is sealed under vacuum with an appropriate inert stopper and the vacuum of the drying apparatus reversed with an inert gas prior to unloading. In either case, the final product is hermetically sealed in an inert gaseous atmosphere.

After rehydration of the ATM (see below), histocompatible, viable cells can be restored to the ATM to produce a permanently accepted graft that may be remodeled by the host. In one embodiment, histocompatible viable cells may be added to the matrices by standard in vitro cell coculturing techniques prior to transplantation, or by in vivo repopulation following transplantation. In vivo repopulation can be by the recipient's own cells migrating into the ATM or by infusing or injecting cells obtained from the recipient or histocompatible cells from another donor into the ATM in situ.

The cell types chosen for reconstitution may depend on the nature of the tissue or organ to which the ATM is being remodeled. For example, the reconstitution of full-thickness skin with an ATM often requires the restoration of epidermal cells or keratinocytes. Thus, cells derived directly from the intended recipient can be used to reconstitute an ATM and the resulting composition grafted to the recipient in the form of a meshed split-skin graft. Alternatively, cultured (autologous or allogeneic) cells can be added to the ATM. Such cells can be, for example, grown under standard tissue culture conditions and then added to the ATM. In another embodiment, the cells can be grown in and/or on an ATM in tissue culture. Cells grown in and/or on an ATM in tissue culture can have been obtained directly from an appropriate donor (e.g., the intended recipient or an allogeneic donor) or they can have been first grown in tissue culture in the absence of the ATM.

The endothelial cell is important for the reconstitution of heart valves and vascular conduits. Such cells line the inner surface of the tissue, and may be expanded in culture. Endothelial cells may also be derived, for example, directly from the intended recipient patient or from umbilical arteries or veins.

Other non-limiting examples of cells that may be used to reconstitute the ATMs of the present disclosure include fibroblasts, embryonic stem cells (ESC), adult or embryonic mesenchymal stem cells (MSC), prochondroblasts, chondroblasts, chondrocytes, pro-osteoblasts, osteocytes, osteoclasts, monocytes, pro-cardiomyoblasts, pericytes, cardiomyoblasts, cardiomyocytes, gingival epithelial cells, or periodontal ligament stem cells. Naturally, the ATM can be repopulated with combinations of two more (e.g., two, three, four, five, six, seven, eight, nine, or ten) of these cell-types.

Reagents and methods for carrying out all the above steps are known in the art. Suitable reagents and methods are described in, for example, U.S. Pat. No. 5,336,616.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical implant, comprising:
   a breast implant; and
   a sample of biocompatible material configured and dimensioned to conform to at least a portion of the breast implant and comprising a first edge consisting essentially of a first convex portion and a second edge consisting essentially of a second convex portion;
   wherein, when the sample of biocompatible material is in a planar configuration, the first convex portion of the first edge defines a first radius of curvature that extends away from the second edge and the second convex portion of the second edge defines a second radius of curvature that extends away from the first edge, the first radius of curvature being different from the second radius of curvature; and
   wherein the first and second edges of the sample of biocompatible material are joined to each other at pointed apexes.

2. The medical implant of claim 1, wherein the sample of biocompatible material is sheet-like in form.

3. The medical implant of claim 1, wherein the sample of biocompatible material comprises a single layer sheet.

4. The medical implant of claim 1, wherein the sample of biocompatible material comprises a multi-layered sheet.

5. The medical implant of claim 1, wherein the first edge includes a straight portion.

6. The medical implant of claim 1, wherein the second edge includes a straight portion.

7. The medical implant of claim 1, wherein the sample of biocompatible material is oversized relative to the breast implant.

8. The medical implant of claim 1, wherein the sample of biocompatible material comprises an acellular tissue matrix.

9. The medical implant of claim 8, wherein the acellular tissue matrix comprises a decellularized collagen-containing tissue matrix from a nonhuman animal.

10. The medical implant of claim 9, wherein the nonhuman animal is a pig.

11. The medical implant of claim 9, wherein the nonhuman animal is genetically modified such that tissues in the nonhuman animal lack galactose α-1,3-galactose epitopes.

12. The medical implant of claim 8, wherein the acellular tissue matrix lacks an epithelial basement membrane.

13. The medical implant of claim 8, wherein the acellular tissue matrix is a dermal tissue matrix.

* * * * *